United States Patent
Kern et al.

(10) Patent No.: US 10,457,915 B2
(45) Date of Patent: Oct. 29, 2019

(54) CHEMICAL DIFFERENTIATION OF PLURIPOTENTSTEM CELLS INTO RETINAL EPITHELIAL CELLS

(71) Applicant: INTERNATIONAL STEM CELL CORPORATION, Carlsbad, CA (US)

(72) Inventors: Russell A. Kern, Carlsbad, CA (US); Rodolfo Gonzalez, Carlsbad, CA (US)

(73) Assignee: International Stem Cell Corporation, Carlsbad, CA (US)

( * ) Notice: Subject to any disclaimer, the term of this patent is extended or adjusted under 35 U.S.C. 154(b) by 0 days.

(21) Appl. No.: 14/712,633

(22) Filed: May 14, 2015

(65) Prior Publication Data

US 2016/0122711 A1    May 5, 2016

Related U.S. Application Data (60) Provisional application No. 61/993,929, filed on May 15, 2014.

(51) Int. Cl.
| | | |
|---|---|---|
| *A61K 35/30* | (2015.01) | |
| *C12N 5/079* | (2010.01) | |
| *A61K 35/545* | (2015.01) | |

(52) U.S. Cl.
CPC ............ *C12N 5/0621* (2013.01); *A61K 35/30* (2013.01); *A61K 35/545* (2013.01); *C12N 2501/15* (2013.01); *C12N 2501/155* (2013.01); *C12N 2501/415* (2013.01); *C12N 2501/727* (2013.01)

(58) Field of Classification Search
CPC .............................. C12N 5/0621; A61K 35/30
See application file for complete search history.

(56) References Cited

U.S. PATENT DOCUMENTS

| | | |
|---|---|---|
| 2011/0223660 A1 | 9/2011 | Park et al. |
| 2013/0195806 A1 | 8/2013 | Gay et al. |

OTHER PUBLICATIONS

Meyers et al (Stem Cells, 29: 1206-1218, 2011).*
Borooah, S. et al.: "*Using Human Induced Pluripotent Stem Cells to Treat Retinal Disease*"; Prog Retin Eye Res., Nov. 2013, vol. 37, No. 100; pp. 163-181.
Hao, J. et al.: "*Dorsomorphin, a Selective Small Molecule Inhibitor of BMP Signaling, Promotes Cardiomyogenesis in Embryonic Stem Cells.*"; PLoS One, Aug. 6, 2008, vol. 3, No. 8, e2904, 7 pgs.
Osakada, F. et al.: "*Drug Development Targeting the Glycogen Synthase Kinase-3-Beta (GSK-3-Beta)-Mediated Signal Transduction Pathway: Targeting the Wnt Pathway and Transplantation Therapy as Strategies for Retinal Repair*"; J Pharmacol Sci., Jan. 29, 2009, vol. 109; pp. 168-173.
Osakada, F et al.: "*In Vitro Differentiation of Retinal Cells From Human Pluripotent Stem Cells by Small-Molecule Induction*"; J Cell Sci., Sep. 1, 2009, vol. 122, No. 17; pp. 3169-3179.
International Search Report dated Aug. 21, 2015, regarding PCT/US2015/030782.

\* cited by examiner

*Primary Examiner* — Anoop K Singh
*Assistant Examiner* — Magdalene K Sgagias
(74) *Attorney, Agent, or Firm* — DLA Piper LLP (US)

(57) ABSTRACT

The present invention is based in part on a chemically defined method of generating retinal epithelial cells and retinal pigmented epithelial cells from human pluripotent stem cells (hpSCs). The present invention also provides methods and kits for treating degenerative eye disorders.

12 Claims, 12 Drawing Sheets

FIG. 7A — POU5F1

FIG. 7B — BEST1 (HESC-derived RPE RT-PCR)

FIG. 7C — OTX2

FIG. 7D — RLBP1

FIG. 7E — RPE65

FIG. 7F — SERPINF1

CHEMICAL DIFFERENTIATION OF PLURIPOTENTSTEM CELLS INTO RETINAL EPITHELIAL CELLS

RELATED APPLICATIONS

This application claims the benefit of priority to U.S. Provisional Patent Application Ser. No. 61/993,929, filed on May 15, 2014. The aforementioned application is expressly incorporated herein by reference in its entirety and for all purposes.

FIELD OF THE INVENTION

The present invention relates to generally to the derivation of retinal epithelial cells and more specifically, to methods for deriving retinal pigmented epithelial cells from human pluripotent stem cells.

BACKGROUND OF THE INVENTION

Human embryonic stem cells (hESCs) cells are pluripotent cells that can differentiate into a large array of cell types. Stem cells are distinguished from other cell types by two important characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

Stem cells have potential in many different areas of health and medical research. Some of the most serious medical conditions, such as cancer and birth defects, are due to problems that occur when cells undergo a transformation. Understanding normal cell development and differentiation mechanisms will allow for a better understanding of these conditions.

Another potential application of stem cells, is making cells and tissues for medical therapies. Today, donated organs and tissues are often used to replace those that are diseased or destroyed. Unfortunately, the number of people needing a transplant far exceeds the number of organs available for transplantation. Stem cells offer the possibility of a renewable source of replacement cells and tissues to treat a myriad of diseases, conditions, and disabilities including Parkinson's disease, amyotrophic lateral sclerosis, spinal cord injury, burns, heart disease, diabetes, and arthritis.

Generation of retinal pigmented epithelial cells (RPEs) from human pluripotent stem cells (hpSCs) is a vital component of cell-based strategies for treatment of degenerative eye diseases. Before hpSC-derived RPEs can be administered in therapeutic modalities, however, chemically defined culture conditions must be developed that reproducibly and robustly induce vascular differentiation. RPEs represent a unique option for the treatment of dry AMD and wet AMD. The methods disclosed herein provide for the generation of a homogenous population of RPEs from hPSCs that can be used for cell therapies of eye disease or drug discovery.

SUMMARY OF THE INVENTION

The present invention is based in part on a chemically defined method of generating retinal epithelial cells and retinal pigmented epithelial cells from human pluripotent stem cells (hpSCs). The present invention also provides methods and kits for treating degenerative eye disorders.

In one embodiment, the present invention is directed to a method of producing retinal pigmented epithelial cells (RPEs) comprising culturing human pluripotent stem cells (hpSCs) on a feeder layer; transferring the hpSCs to feeder layer free culture conditions; culturing the hpSCs with at least one retinal cell inducing agent to produce retinal epithelial progenitor cells; and culturing the retinal epithelial progenitor cells with a glycogen synthase kinase 3 (GSK-3) inhibitor, thereby producing RPEs. In one aspect the hpSCs are embryonic stem cells, parthenogenetic stem cells, induced pluripotent stem cells or nuclear transfer derived stem cells. In another aspect, the feeder layer comprises mitomycin-C inactivated mouse embryonic fibroblast cells. In an additional aspect, the feeder layer free culture conditions comprise culturing the hpSCs on plates coated with a xeno-free substrate.

In a further aspect, the at least one retinal cell inducing agent is a TGFβR-1 inhibitor, a Wnt inhibitor, a BMP inhibitor, a ROCK inhibitor, or any combination thereof. In an aspect, the TGFβR-1 inhibitor is A83-01, D4476, GW788388, ITD1, LY2109761, Galunisertib (LY2157299), LY364947, 8268712, RepSox, SB431542, SB505124, SB525334, SD-208 or SIS3. In certain aspects, the Wnt inhibitor is Cardionogen 1, Calphostin C, CCT031374 hydrobromide, FH535, ICG-001, iCRT14, IWP-2, IWP-4, IWP-12, IWP-L6, IWR-1, JW55, JW67, KY02111, LGK-974, MN64, PNU74654, QS11, TAK715, TC-E5001, WAY316606 hydrochloride, WIKI4, WNT-059 or XAV-939. In another aspect, the BMP inhibitor is Dorsomorphin, LD-193189, DMH-1 or K02288. In one aspect, the ROCK inhibitor is AS1892802, AT13148, Fasudil (HA-1077); Glycyl-H-1152, GSK269962, GSK429286, HA-1100, H1152, Narciclasin, OXA06, OXA06 dihydrochloride, RKI-1447, SB772077B, SR3677, Thiazovivin or Y-276322. In an additional aspect, the GSK-3 inhibitor is 3F8, 1-Azakenpaullone, 10Z-Humenialdisine, Alsterpaullone, A1070722, AR-A014418, AZD1080, AZD2858, Bikinin, BIO, Cazpaullone, CT98014, CT98023, CT99021 (Chir99021), Chir98014, Dibromocantharelline, GSKJ2, HMK-32, Hymenialdesine, Indirubin, Indirubin-3'-omime, IM-12, Kenpaullone, L803, L803-mts, Lithium carbonate, LY2090314, Manzamine A, Meridianin, NCS693868, NP00111, NP031115, Palinurine, SB216763, SB415286, TCS21311, TC-G-24, TCS2002, TDZD-8, Tideglusib, Tricantine or TWS119. In a specific aspect, the at least one retinal cell inducing agent comprises SB431542, IWR-1, DMH-1 or Y-27632, or any combination thereof, and the GSK-3 inhibitor comprises Chir90221.

In a further aspect, the hpSCs are cultured with the at least one retinal cell inducing agent for at least about 5 days, at least about 10 days, at least about 11 days, at least about 12 days, at least about 13 days, at least about 14 days or at least about 15 days. In a specific aspect, the hpSCs are cultured with the at least one retinal cell inducing agent for about 12 days. In an aspect, the hpSCs are cultured with the GSK-3 inhibitor for at least about 5 days, at least about 10 days, at least about 11 days, at least about 12 days, at least about 13 days, at least about 14 days or at least about 15 days.

In one aspect, the method further comprises detecting the presence of RPE specific protein expression and/or gene marker expression. In certain aspects the RPE protein expression is MITF, ZO-1, BEST-1 or Melanosome, or a combination thereof. In another aspect, the RPE specific gene marker expression is POU5F1, BEST-1, MITF, OTX2, RLPB1, RPE 65 or SERPINF1, or a combination thereof.

In another embodiment, the present invention provides for retinal pigmented epithelial.

In a further embodiment, the present invention provides a method of treating a subject diagnosed with a degenerative eye disorder comprising administering retinal pigmented epithelial cells to a subject in need thereof. In one aspect, the retinal pigmented epithelial cells are produced by a method comprising culturing hpSCs on a feeder layer; transferring the hpSCs to feeder layer free culture conditions; culturing the hpSCs with at least one retinal cell inducing agent to produce retinal epithelial progenitor cells; and culturing the retinal epithelial progenitor cells with a GSK-3 inhibitor, thereby producing retinal pigmented epithelial cells. In an aspect, the hpSCs are embryonic stem cells, parthenogenetic stem cells, induced pluripotent stem cells or nuclear transfer derived stem cells. In certain aspects, the feeder layer comprises mitomycin-C inactivated mouse embryonic fibroblast cells and the feeder layer free culture conditions comprise culturing the hpSCs on plates coated with a xeno-free substrate. In another aspect, the at least one retinal cell inducing agent is a TGFβR-1 inhibitor, a Wnt inhibitor, a BMP inhibitor or a ROCK inhibitor, or any combination thereof. In a specific aspect, the at least one retinal cell inducing agent comprises SB431542, IWR-1, DMH-1 or Y-27632, or any combination thereof, and the GSK-3 inhibitor is CHIR90221. In a further aspect, the degenerative eye disorder is macular degeneration.

In a further embodiment, the present invention provides for a kit for the derivation of RPEs from hpSCs comprising at least one retinal cell inducing agent; a GSK-3 inhibitor; and directions for the derivation of RPEs from hpSCs. In one aspect, the at least one retinal cell inducing agent is a TGFβR-1 inhibitor, a Wnt inhibitor, a BMP inhibitor or a ROCK inhibitor, or any combination thereof. In another aspect, the at least one retinal cell inducing agent comprises SB431542, IWR-1, DMH-1, or Y-27632, or any combination thereof, and the GSK-3 inhibitor is Chir90221.

In an additional embodiment, the present invention provides a method of producing retinal pigmented epithelial progenitor cells comprising culturing human pluripotent stem cells (hpSCs) on a feeder layer; transferring the hpSCs to feeder layer free culture conditions; and culturing the hpSCs with at least one retinal cell inducing agent, thereby producing retinal epithelial progenitor cells. In one aspect, the hpSCs are selected from the group consisting of: embryonic stem cells, parthenogenetic stem cells, induced pluripotent stem cells and nuclear transfer derived stem cells. In another aspect, the at least one retinal cell inducing agent is a TGFβR-1 inhibitor, a Wnt inhibitor, a BMP inhibitor or a ROCK inhibitor, or any combination thereof. In an additional aspect, the TGFβR-1 inhibitor is A83-01, D4476, GW788388, ITD1, LY2109761, Galunisertib (LY2157299), LY364947, R268712, RepSox, SB431542, SB505124, SB525334, SD-208 or SIS3. In an aspect, the Wnt inhibitor is Cardionogen 1, Calphostin C, CCT031374 hydrobromide, FH535, ICG-001, iCRT14, IWP-2, IWP-4, IWP-12, IWP-L6, IWR-1, JW55, JW67, KY02111, LGK-974, MN64, PNU74654, QS11, TAK715, TC-E5001, WAY316606 hydrochloride, WIKI4, WNT-C59 or XAV-939. In a further aspect, the BMP inhibitor is Dorsomorphin, LD-193189, DMH-1 or K02288. In one aspect, the ROCK inhibitor is AS1892802, AT13148, Fasudil (HA-1077); Glycyl-H-1152, GSK269962, GSK429286, HA-1100, H1152, Narciclasin, OXA 06, OXA06 dihydrochloride, RKI-1447, SB772077B, SR3677, Thiazovivin or Y-27632.

DETAILED DESCRIPTION OF THE INVENTION

The present invention is based in part on a chemically defined method of generating retinal epithelial cells and retinal pigmented epithelial cells from human pluripotent stem cells (hpSCs). The present invention also provides methods and kits for treating degenerative eye disorders.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

As used in this specification and the appended claims, the singular forms "a", "an", and "the" include plural references unless the context clearly dictates otherwise. Thus, for example, references to "the method" includes one or more methods, or steps of the type described herein which will become apparent to those persons skilled in the art upon reading this disclosure and so forth.

Degenerative eye diseases and disorders are common as people age. Macular degeneration is a chronic medical condition that usually affects older adults and results in a loss of vision in the center of the visual field because of damage to the retina. It occurs in "dry" and "wet" forms. It is a major cause of blindness and visual impairment in older adults, afflicting 30-50 million people globally. Macular degeneration can make it difficult or impossible to read or recognize faces, although enough peripheral vision remains to allow other activities of daily life. There are few treatment options for patients suffering from either dry AMD or wet AMD.

In the dry form (dry AMD), cellular debris called drusen accumulates between the retina and the choroid, causing atrophy and scarring to the retina. No medical or surgical treatment is available for dry AMD; however, recent clinical trials found some benefit with some vitamin supplements along with high doses of antioxidants.

In the wet form (wet AMD) blood vessels grow up from the choroid behind the retina which can leak exudate and fluid and also cause hemorrhaging. It can be treated with laser coagulation, and more commonly with medication that stops and sometimes reverses the growth of blood vessels. Wet AMD causes vision loss due to abnormal blood vessel growth (choroidal neovascularization) in the choriocapillaris, through Bruch's membrane. The proliferation of abnormal blood vessels in the retina is stimulated by vascular endothelial growth factor (VEGF). Unfortunately, these new vessels are fragile, ultimately leading to blood and protein leakage below the macula. Bleeding, leaking, and scarring from these blood vessels eventually cause irreversible damage to the photoreceptors and rapid vision loss if left untreated.

Generation of retinal pigmented epithelial cells (RPEs) from human pluripotent stem cells (hpSCs), including but not limited to human embryonic stem cells (hESCs), human parthenogenetic stem cells (hPSCs), nuclear transfer derived stem cells, and induced pluripotent stem cells (IPSCs), is a vital component of cell-based strategies for treatment of degenerative eye disease and disorders. Before hpSC-derived RPEs can be administered in therapeutic modalities, however, chemically defined culture conditions must be developed that reproducibly and robustly induce the generation of RPEs. Here, a process was identified using a combination of retinal cell inducing agents and GSK-3 inhibitors to develop a chemically defined differentiation method to differentiate hpSCs into RPEs.

The methods of deriving retinal pigmented epithelial cells (RPEs) described herein are produced from human pluripotent stem cells (hpSCs), such as embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Human stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

As used herein, "multipotent" or "multipotent cell" refers to a cell type that can give rise to a limited number of other particular cell types. Examples of multipotent cells include ectodermal cells, endodermal cells, mesodermal cells and neural stem cells which can give rise to limited number of other cells.

As used herein, a "pluripotent cell" refers to a cell that can be maintained in vitro for prolonged, theoretically indefinite period of time in an undifferentiated state, that can give rise to different differentiated tissue types, i.e., ectoderm, mesoderm, and endoderm. Human pluripotent stem cells (hpSCs) include, but are not limited to, human embryonic stem cells, human parthenogenetic stem cells, nuclear transfer derived stem cells and induced pluripotent stem cells. Methods of obtaining such hpSCs are well known in the art.

One method of obtaining hpSCs is by parthenogenesis. "Parthenogenesis" ("parthenogenically activated" and "parthenogenetically activated" is used herein interchangeably) refers to the process by which activation of the oocyte occurs in the absence of sperm penetration, and refers to the development of an early stage embryo comprising trophectoderm and inner cell mass that is obtained by activation of an oocyte or embryonic cell, e.g., blastomere, comprising DNA of all female origin. In a related aspect, a "parthenote" refers to the resulting cell obtained by such activation. In another related aspect, "blastocyst: refers to a cleavage stage of a fertilized of activated oocyte comprising a hollow ball of cells made of outer trophoblast cells and an inner cell mass (ICM). In a further related aspect, "blastocyst formation" refers to the process, after oocyte fertilization or activation, where the oocyte is subsequently cultured in media for a time to enable it to develop into a hollow ball of cells made of outer trophoblast cells and ICM (e.g., 5 to 6 days).

Another method of obtaining hpSCs is through nuclear transfer. As used herein, "nuclear transfer" refers to the fusion or transplantation of a donor cell or DNA from a donor cell into a suitable recipient cell, typically an oocyte of the same or different species that is treated before, concomitant or after transplant or fusion to remove or inactivate its endogenous nuclear DNA. The donor cell used for nuclear transfer include embryonic and differentiated cells, e.g., somatic and germ cells. The donor cell may be in a proliferative cell cycle (G1, G2, S or M) or non-proliferating (G0 or quiescent). Preferably, the donor cell or DNA from the donor cell is derived from a proliferating mammalian cell culture, e.g., a fibroblast cell culture. The donor cell optionally may be transgenic, i.e., it may comprise one or more genetic addition, substitution or deletion modifications.

A further method for obtaining hpSCs is through the reprogramming of cells to obtain induced pluripotent stem cells. Takahashi et al. (Cell 131, 861-872 (2007)) have disclosed methods for reprogramming differentiated cells, without the use of any embryo or ES (embryonic stem) cell, and establishing an inducible pluripotent stem cell having similar pluripotency and growing abilities to those of an ES cell. Nuclear reprogramming factors for differentiated fibroblasts include products of the following four genes: an Oct family gene; a Sox family gene; a Klf family gene; and a Myc family gene.

The pluripotent state of the cells is preferably maintained by culturing cells under appropriate conditions, for example, by culturing on a fibroblast feeder layer or another feeder layer or culture that includes leukemia inhibitory factor (LIF). The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

The pluripotent state of the cells used in the present invention can be confirmed by various methods. For example, the cells can be tested for the presence or absence of characteristic ES cell markers. In the case of human ES cells, examples of such markers are identified supra, and include SSEA-4, SSEA-3, TRA-1-60, TRA-1-81 and OCT 4, and are known in the art.

Also, pluripotency can be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types.

Yet another method of confirming pluripotency is to observe ES cell differentiation into embryoid bodies and other differentiated cell types when cultured under conditions that favor differentiation (e.g., removal of fibroblast feeder layers). This method has been utilized and it has been confirmed that the subject pluripotent cells give rise to embryoid bodies and different differentiated cell types in tissue culture.

The resultant pluripotent cells and cell lines, preferably human pluripotent cells and cell lines have numerous therapeutic and diagnostic applications. Such pluripotent cells may be used for cell transplantation therapies or gene therapy (if genetically modified) in the treatment of numerous disease conditions.

Human pluripotent stem cells (hpSCs) include, but are not limited to, human embryonic stem cells (hESCs), human parthenogenetic stem cells (hPSCs), nuclear transfer derived stem cells, induced pluripotent stem cells (IPSCs) and cell lines produced by such cells. hpSCs are maintained in culture in a pluripotent state by routine passage until it is desired that neural stem cells be derived.

The present invention provides methods for the derivation of retinal pigmented epithelial cells (RPEs) by treating hpSCs with at least one retinal cell induction agent and at least one GSK-3 inhibitor.

Retinal cell inducing agents include transforming growth factor β receptor 1 (TGFβR-1) inhibitors, Wnt inhibitors, bone morphogenic protein (BMP) inhibitors and rho-associated protein kinase (ROCK) inhibitors.

TGFβ receptors are single pass serine/threonine kinase receptors. Transforming growth factor, beta receptor I (TGFβR1) forms a heteromeric complex with type II TGF-beta receptors when bound to TGF-beta, transducing the TGF-beta signal from the cell surface to the cytoplasm.

TGFβR1 inhibitors include, but are not limited to A83-01, D4476, GW788388, ITD1, LY2109761, Galunisertib (LY2157299), LY364947, 8268712, RepSox, SB431542, SB505124, SB525334, SD-208 and SIS3.

The Wnt family of signaling proteins influences most aspects of metazoan embryonic development and post-embryonic tissue homeostasis1. Cellular responses to these proteins are often categorized based on their utilization of β-catenin, a co-activator of the TCF/LEF family of transcriptional effectors. Similar to other signal transduction pathways required for cell fate decision-making, activity of the Wnt/β-catenin ("canonical") pathway maintains transcriptional programs that enable stem cells to remain multipotent. Inability to sustain these transcription programs results in compromised ability of stem cells to self-renew. Hyperactivation of the Wnt/β-catenin pathway is thought to induce premature senescence of stem cells and age-related loss of stem cell function. In cancer, hyperactivation of the Wnt/β-catenin pathway, often in conjunction with mutations in other cell growth regulatory genes, can lead to aberrant cell growth.

Wnt/βcatenin inhibitors include, but are limited to, Cardionogen 1, Calphostin C, CCT031374 hydrobromide, FH535, ICG-001, iCRT14, IWP-2, IWP-4, IWP-12, IWP-L6, IWR-1, JW55, JW67, KY02111, LGK-974, MN64, PNU74654, QS11, TAK715, TC-E5001, WAY316606 hydrochloride, WIKI4, WNT-059 and XAV-939.

Bone morphogenic proteins (BMPs) are multi-functional growth factors that belong to the transforming growth factor beta (TGFβ) superfamily. Originally discovered by their ability to induce the formation of bone and cartilage, BMPs are now considered to constitute a group of pivotal morphogenetic signals, orchestrating tissue architecture throughout the body. They have an important role during embryonic development on the embryonic patterning and early skeletal formation. BMP signaling plays critical roles in heart, neural and cartilage development.

Examples of BMP inhibitors include, but are not limited to, Dorsomorphin, LD-193189, DMH-1 and K02288.

Rho-associated protein kinase (ROCK) is a kinase belonging to the AGC (PKA/PKG/PKC) family of serine-threonine kinases. It is involved mainly in regulating the shape and movement of cells by acting on the cytoskeleton. Recent research has shown that ROCK signaling plays an important role in many diseases including diabetes, neurodegenerative diseases such as Parkinson's disease and amyotrophic lateral sclerosis, pulmonary hypertension and cancer.

ROCK inhibitors include, but are not limited to, AS1892802, AT13148, Fasudil (HA-1077); Glycyl-H-1152, GSK269962, GSK429286, HA-1100, H1152, Narciclasin, OXA 06, OXA06 dihydrochloride, RKI-1447, SB772077B, SR3677, Thiazovivin and Y-27632.

Glycogen synthase kinase 3 (GSK-3) is a serine/threonine protein kinase that mediates the addition of phosphate molecules onto serine and threonine amino acid residues. First discovered in 1980 as a regulatory kinase for its namesake, Glycogen synthase, GSK-3 has since been identified as a kinase for over forty different proteins in a variety of different pathways. In mammals GSK-3 is encoded by two known genes, GSK-3 alpha (GSK3A) and GSK-3 beta (GSK3B). GSK-3 has recently been the subject of much research because it has been implicated in a number of diseases, including Type II diabetes (Diabetes mellitus type 2), Alzheimer's Disease, inflammation, cancer, and bipolar disorder.

Inhibitors of GSK-3 include, but are not limited to, 3F8, 1-Azakenpaullone, 10Z-Humenialdisine, Alsterpaullone, A1070722, AR-A014418, AZD1080, AZD2858, Bikinin, BIO, Cazpaullone, CT98014, CT98023, CT99021 (Chir99021), Chir98014, Dibromocantharelline, GSKJ2, HMK-32, Hymenialdesine, Indirubin, Indirubin-3'-omime, IM-12, Kenpaullone, L803, L803-mts, Lithium carbonate, LY2090314, Manzamine A, Meridianin, NCS693868, NP00111, NP031115, Palinurine, SB216763, SB415286, TCS21311, TC-G-24, TCS2002, TDZD-8, Tideglusib, Tricantine and TWS119.

The production of RPEs can be verified by detecting RPE specific protein expression and gene marker expression. RPE specific protein expression can be detected by immunohistochemistry, FACs analysis or any other method known in the art. RPE specific proteins include, but are not limited to, microphthalmia-associated transcription factor (MITF), ZO-1, bestrophin 1 (BEST-1) or Melannosome (Mel). RPE specific gene marker expression can be detected by nucleic acid amplification, nucleic acid hybridization, RT-PCR or any other method known in the art. RPE specific gene markers include, but are not limited to, POU5F1, BEST-1, MITF, OTX2, RLPB1, RPE 65 or SERPINF1.

In one embodiment, the present invention is directed to a method of producing retinal pigmented epithelial cells (RPEs) comprising culturing human pluripotent stem cells (hpSCs) on a feeder layer; transferring the hpSCs to feeder layer free culture conditions; culturing the hpSCs with at least one retinal cell inducing agent to produce retinal progenitor cells; and culturing the retinal progenitor cells with a glycogen synthase kinase 3 (GSK-3) inhibitor, thereby producing RPEs. In one aspect the retinal progenitor cells are embryonic stem cells, parthenogenetic stem cells, induced pluripotent stem cells or nuclear transfer derived stem cells. In another aspect, the feeder layer comprises mitomycin-C inactivated mouse embryonic fibroblast cells. In an additional aspect, the feeder layer free culture conditions comprise culturing the hpSCs on plates coated with a xeno-free substrate.

In a further aspect, the at least one retinal cell inducing agent is a TGFβR-1 inhibitor, a Wnt inhibitor, a BMP inhibitor, a ROCK inhibitor, or any combination thereof. In an aspect, the TGFβR-1 inhibitor is A83-01, D4476, GW788388, ITD1, LY2109761, Galunisertib (LY2157299), LY364947, 8268712, RepSox, SB431542, SB505124, SB525334, SD-208 or SIS3. In certain aspects, the Wnt inhibitor is Cardionogen 1, Calphostin C, CCT031374 hydrobromide, FH535, ICG-001, iCRT14, IWP-2, IWP-4, IWP-12, IWP-L6, IWR-1, JW55, JW67, KY02111, LGK-974, MN64, PNU74654, QS11, TAK715, TC-E5001, WAY316606 hydrochloride, WIKI4, WNT-059 or XAV-939. In another aspect, the BMP inhibitor is Dorsomorphin, LD-193189, DMH-1 or K02288. In one aspect, the ROCK inhibitor is AS1892802, AT13148, Fasudil (HA-1077); Glycyl-H-1152, GSK269962, GSK429286, HA-1100, H1152, Narciclasin, OXA 06, OXA06 dihydrochloride, RKI-1447, SB772077B, SR3677, Thiazovivin or Y-27632. In an additional aspect, the GSK-3 inhibitor is 3F8, 1-Azakenpaullone, 10Z-Humenialdisine, Alsterpaullone, A1070722, AR-A014418, AZD1080, AZD2858, Bikinin, BIO, Cazpaullone, CT98014, CT98023, CT99021 (Chir99021), Chir98014, Dibromocantharelline, GSKJ2, HMK-32, Hymenialdesine, Indirubin, Indirubin-3'-omime, IM-12, Kenpaullone, L803, L803-mts, Lithium carbonate, LY2090314, Manzamine A, Meridianin, NCS693868, NP00111, NP031115, Palinurine, SB216763, SB415286, TCS21311, TC-G-24, TCS2002, TDZD-8, Tideglusib, Tricantine or TWS119. In a specific aspect, the at least one retinal cell inducing agent comprises SB431542, IWR-1, DMH-1 or Y-27632, or any combination thereof, and the GSK-3 inhibitor comprises Chir90221.

In a further aspect, the hpSCs are cultured with the at least one retinal cell inducing agent for at least about 5 days, at least about 10 days, at least about 11 days, at least about 12 days, at least about 13 days, at least about 14 days or at least about 15 days. In a specific aspect, the hpSCs are cultured with the at least one retinal cell inducing agent for about 12 days. In an aspect, the hpSCs are cultured with the GSK-3 inhibitor for at least about 5 days, at least about 10 days, at least about 11 days, at least about 12 days, at least about 13 days, at least about 14 days or at least about 15 days.

In one aspect, the method further comprises detecting the presence of RPE specific protein expression and/or gene marker expression. In certain aspects the RPE specific protein expression is MITF, ZO-1, BEST-1 or Melanosome, or a combination thereof. In another aspect, the RPE specific gene marker expression is POU5F1, BEST-1, MITF, OTX2, RLPB1, RPE 65 or SERPINF1, or a combination thereof.

In another embodiment, the present invention provides for retinal pigmented epithelial.

In a further embodiment, the present invention provides a method of treating a subject diagnosed with a degenerative eye disorder comprising administering retinal pigmented epithelial cells to a subject in need thereof. In one aspect, the retinal pigmented epithelial cells are produced by a method comprising culturing hpSCs on a feeder layer; transferring the hpSCs to feeder layer free culture conditions; culturing the hpSCs with at least one retinal cell inducing agent to produce retinal epithelial progenitor cells; and culturing the retinal epithelial progenitor cells with a GSK-3 inhibitor, thereby producing retinal pigmented epithelial cells. In an aspect, the hpSCs are embryonic stem cells, parthenogenetic stem cells, induced pluripotent stem cells or nuclear transfer derived stem cells. In certain aspects, the feeder layer comprises mitomycin-C inactivated mouse embryonic fibroblast cells and the feeder layer free culture conditions comprise culturing the hpSCs on plates coated with a xeno-free substrate. In another aspect, the at least one retinal cell inducing agent is a TGFβR-1 inhibitor, a Wnt inhibitor, a BMP inhibitor or a ROCK inhibitor, or any combination thereof. In a specific aspect, the at least one retinal cell inducing agent comprises SB431542, IWR-1, DMH-1 or Y-27632, or any combination thereof, and the GSK-3 inhibitor is Chir90221. In a further aspect, the degenerative eye disorder is macular degeneration.

In a further embodiment, the present invention provides for a kit for the derivation of RPEs from hpSCs comprising at least one retinal cell inducing agent; a GSK-3 inhibitor; and directions for the derivation of RPEs from hpSCs. In one aspect, the at least one retinal cell inducing agent is a TGFβR-1 inhibitor, a Wnt inhibitor, a BMP inhibitor or a ROCK inhibitor, or any combination thereof. In another aspect, the at least one retinal cell inducing agent comprises SB431542, IWR-1, DMH-1, or Y-27632, or any combination thereof, and the GSK-3 inhibitor is Chir90221.

In an additional embodiment, the present invention provides a method of producing retinal pigmented epithelial progenitor cells comprising culturing human pluripotent stem cells (hpSCs) on a feeder layer; transferring the hpSCs to feeder layer free culture conditions; and culturing the hpSCs with at least one retinal cell inducing agent, thereby producing retinal epithelial progenitor cells. In one aspect, the hpSCs are selected from the group consisting of: embryonic stem cells, parthenogenetic stem cells, induced pluripotent stem cells and nuclear transfer derived stem cells. In another aspect, the at least one retinal cell inducing agent is a TGFβR-1 inhibitor, a Wnt inhibitor, a BMP inhibitor or a ROCK inhibitor, or any combination thereof. In an additional aspect, the TGFβR-1 inhibitor is A83-01, D4476, GW788388, ITD1, LY2109761, Galunisertib (LY2157299), LY364947, R268712, RepSox, SB431542, SB505124, SB525334, SD-208 or SIS3. In an aspect, the Wnt inhibitor is Cardionogen 1, Calphostin C, CCT031374 hydrobromide, FH535, ICG-001, iCRT14, IWP-2, IWP-4, IWP-12, IWP-L6, IWR-1, JW55, JW67, KY02111, LGK-974, MN64, PNU74654, QS11, TAK715, TC-E5001, WAY316606 hydrochloride, WIKI4, WNT-C59 or XAV-939. In a further aspect, the BMP inhibitor is Dorsomorphin, LD-193189, DMH-1 or K02288. In one aspect, the ROCK inhibitor is AS1892802, AT13148, Fasudil (HA-1077); Glycyl-H-1152, GSK269962, GSK429286, HA-1100, H1152, Narciclasin, OXA 06, OXA06 dihydrochloride, RKI-1447, SB772077B, SR3677, Thiazovivin or Y-27632.

As described in the Examples below, the presently described methods have been used to successful derive RPE from a variety of hpSCs (i.e. hPSC, hESC and IPSC). The derivation of the RPE was confirmed by protein staining for RPE specific protein expression (i.e. MITF, ZO-1, BEST-1 and Melanosome) and RT-PCR analysis for RPE specific gene markers (POU5F1, BEST1, MITF, OTX2, RLPB1, RPE 65 and SERPINF1). The purity of the derived RPE was demonstrated by FACs analysis.

The invention in all its aspects is illustrated further in the following Examples. The Examples do not, however, limit the scope of the invention, which is defined by the appended claims.

EXAMPLES

Example 1

Growth of hpSCs

The hpSCs maintained on mitomycin-C inactivated mouse embryonic fibroblast feeder layer in embryonic stem medium: Knock Out DMEM/F12, 2 mM L-glutamine, 0.1 mM MEM nonessential amino acids, 0.1 mM β-mercaptoethanol, penicillin/streptomycin/amphotericin B (100 U/100 μg/250 ng) and 5 ng/ml bFGF. Cells were passaged with dispase or collagenase IV every 5-7 days with split ratio of 1:4 or 1:6. The hpSCs were then transferred to CellStart coated plates and grown with Essential 8 medium.

Example 2

Figure 1A:
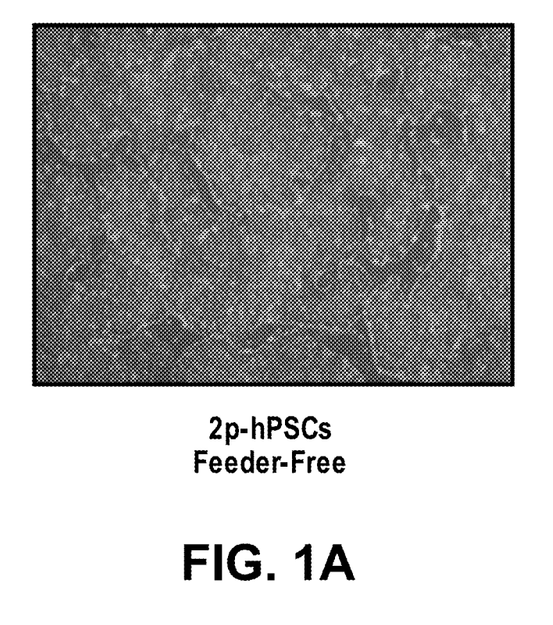
FIGS. 1A-C show the development of retinal pigmented epithelial cells. A. hPSCs grown under feeder free conditions. B. hPSCs treated with IWR-1, SB431542 and DMH-1 for 12 days. C. hPSCs treated with CHIR99021 for 15 days.
Figure 1B:
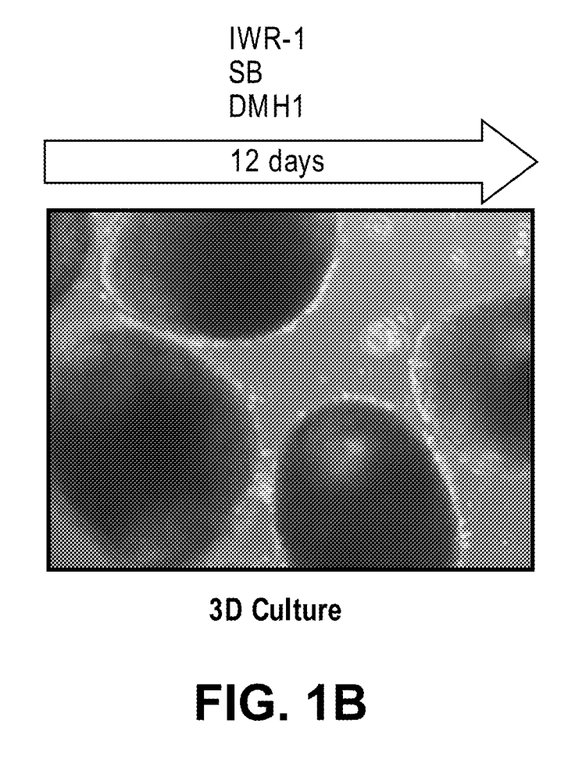
Figure 1C:
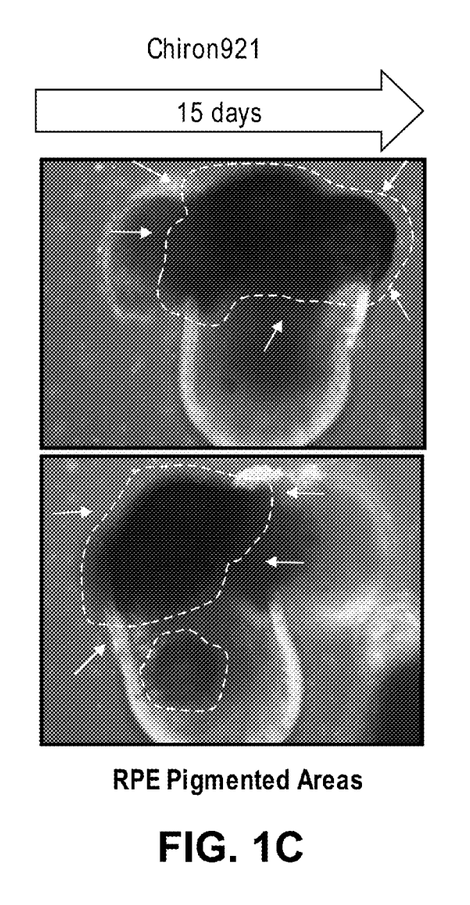
Figure 2:
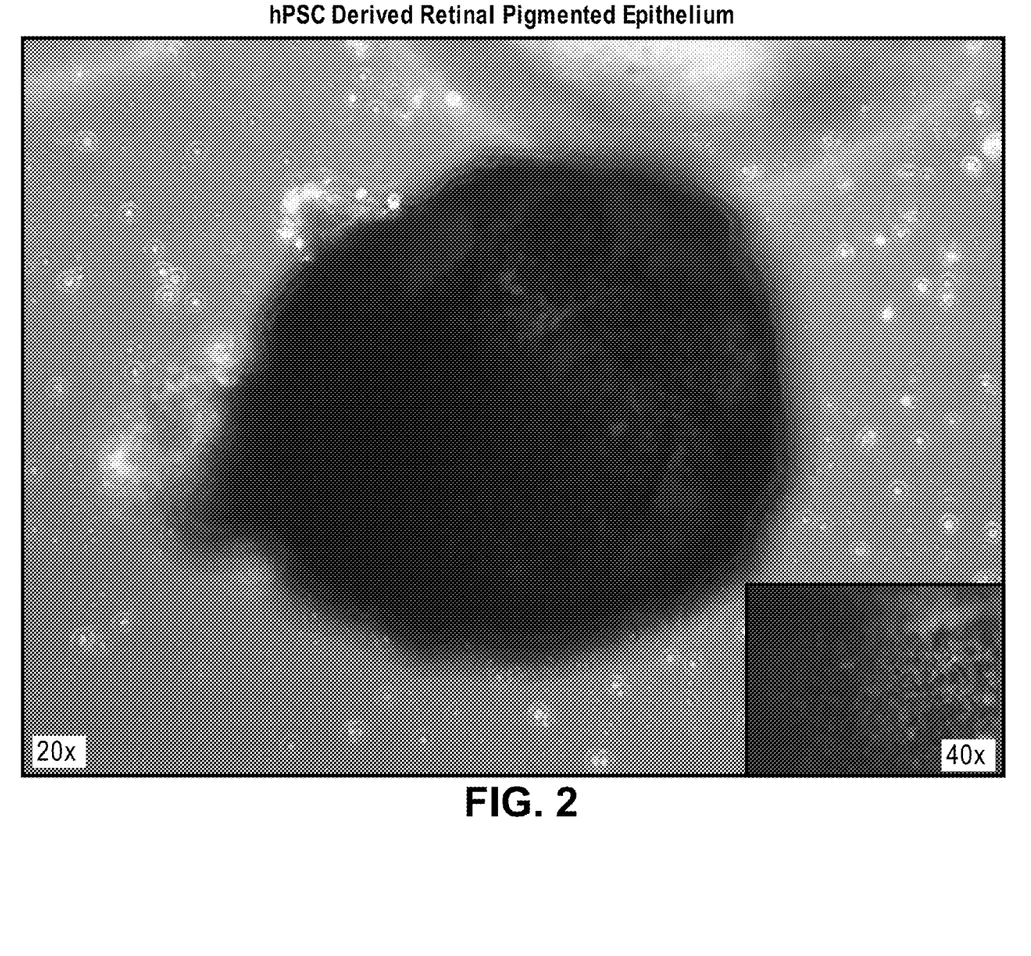
FIG. 2 shows phase contrast images (20× and 40× magnification) of hpSC derived a retinal pigmented epithelial cells.
Figure 3A:
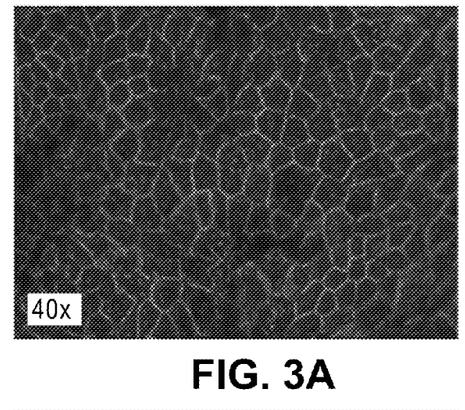
FIGS. 3A-D show protein expression analysis of human parthenogenetic stem cell derived retinal pigmented epithelial cells (hPSC-derived RPE). A. Phase-Contrast image of a culture of hPSC-derived RPE after chemical differentiation. B-D. Immunocytochemistry images of hPSC-derived RPE cells stained for RPE-specific marker protein expression (B) MITF, and ZO-1, (C) Best-1 and ZO-1, and (D) Melanosome and ZO-1.
Figure 3B:
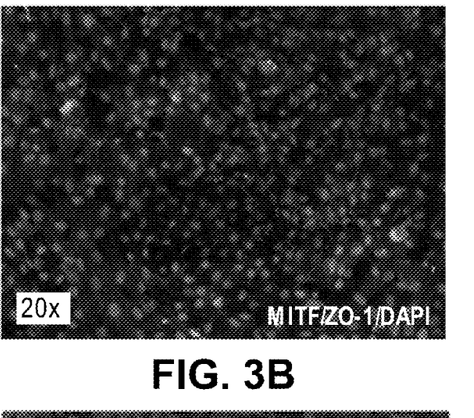
Figure 3C:
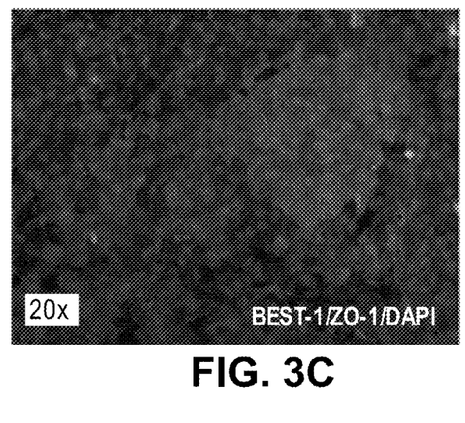
Figure 3D:
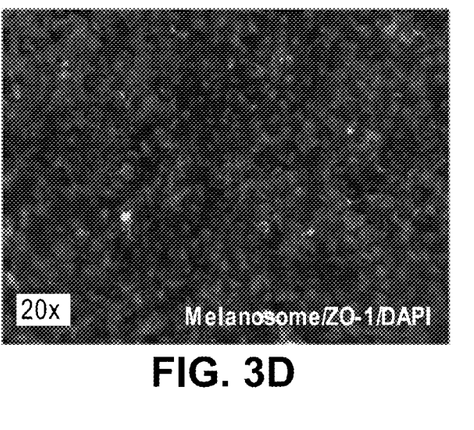
Figure 4A:
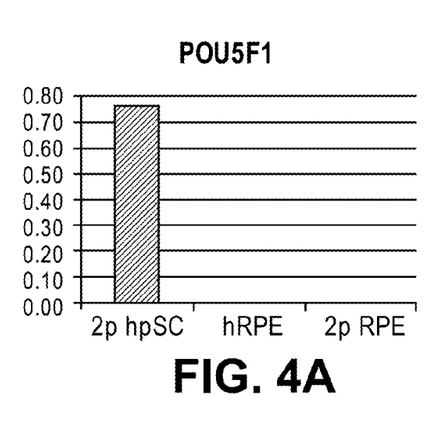
FIGS. 4A-F show RT-PCR gene expression analysis of human parthenogenetic stem cell derived retinal pigmented epithelial cells (hPSC-derived RPE) for RPE specific genes: (A) POU5F1, (B) BEST1, (C) OTX2, (D) RLBP1, (E) RPE65 and (F) SERPINF1.
Figure 4B:
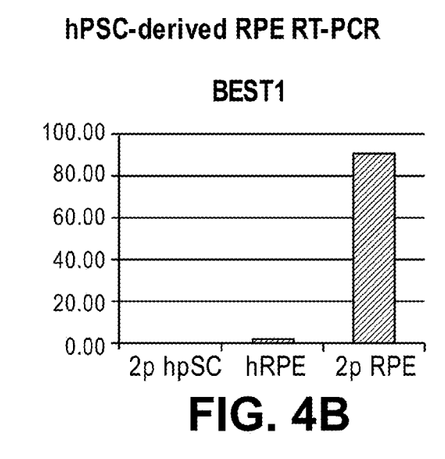
Figure 4C:
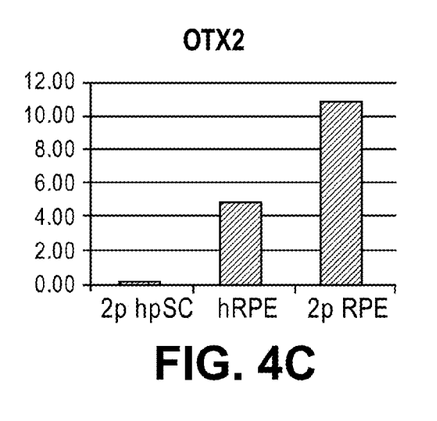
Figure 4D:
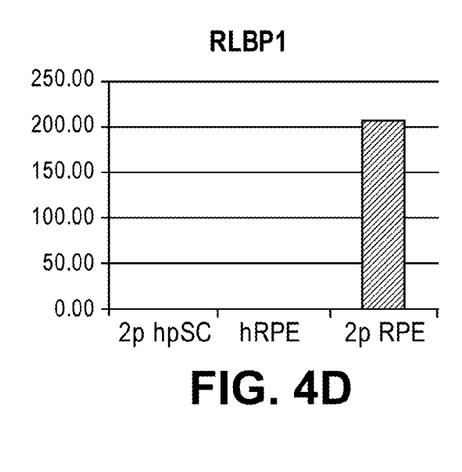
Figure 4E:
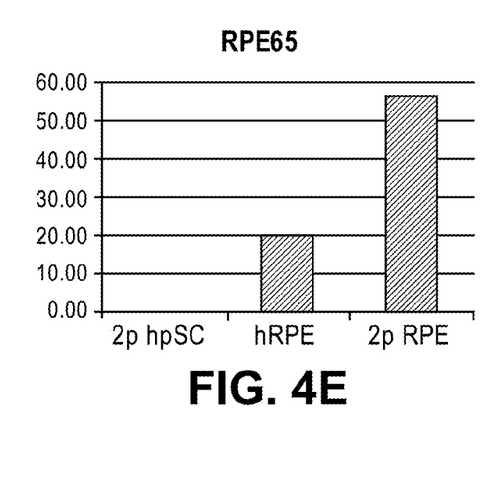
Figure 4F:
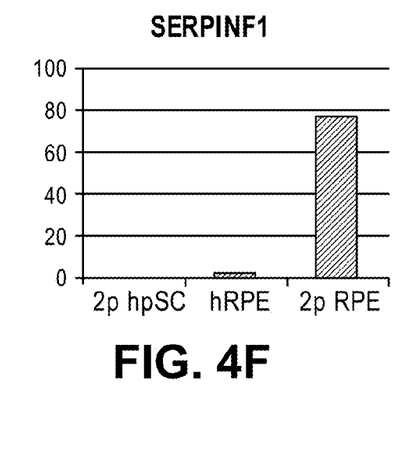
Figure 5A:
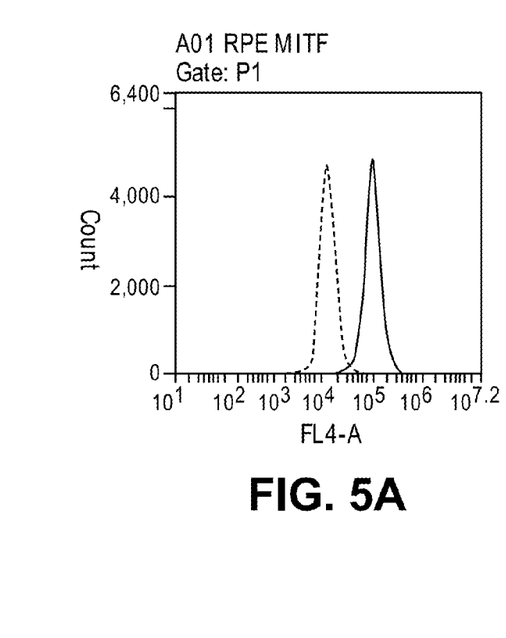
FIGS. 5A-C show purity assessment of hPSC derived retinal pigmented epithelial cells (hPSC-derived RPE) by FACs analysis for RPE-specific proteins (A) MITF, (B) Mel and (C) BEST-1 (right curves) and Isotype control (left curves).
Figure 5B:
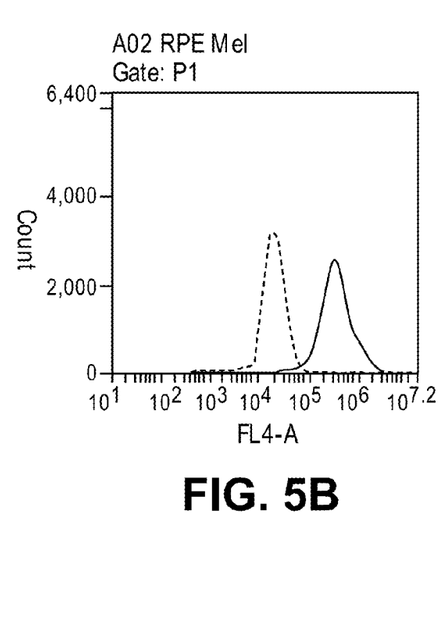
Figure 5C:
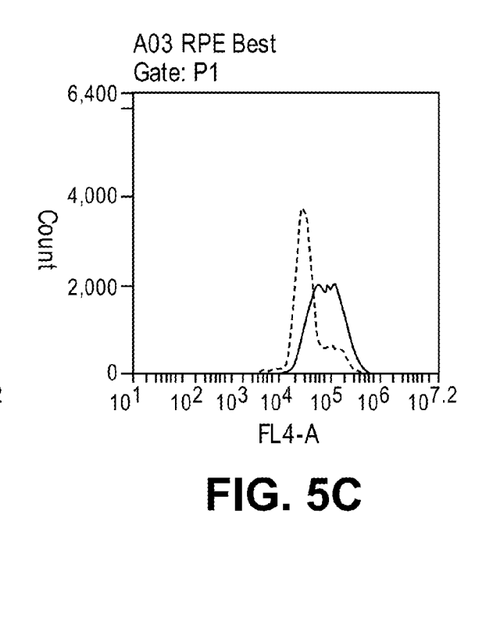
Figure 6A:
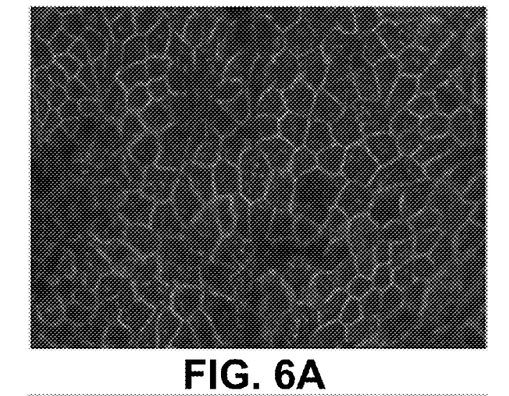
FIGS. 6A-D show protein expression analysis of human embryonic stem cell derived retinal pigmented epithelium (hESC-derived RPE). A. Phase-Contrast image of a culture of hESC-derived RPE after chemical differentiation. B-D. Immunocytochemistry images of hESC-derived RPE cells stained for RPE-specific marker protein expression (B) MITF, and ZO-1, (C) Best-1 and ZO-1, and (D) Melanosome and ZO-1.
Figure 6B:
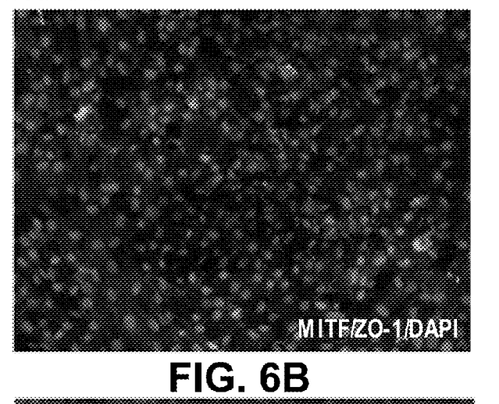
Figure 6C:
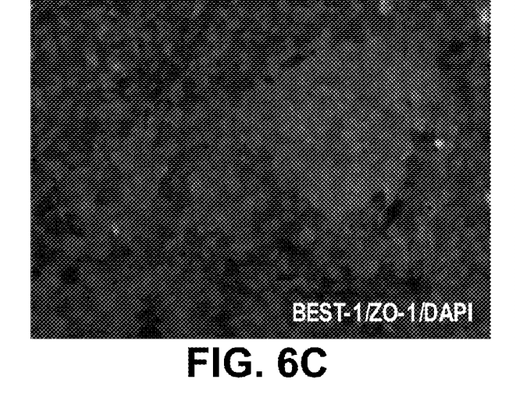
Figure 6D:
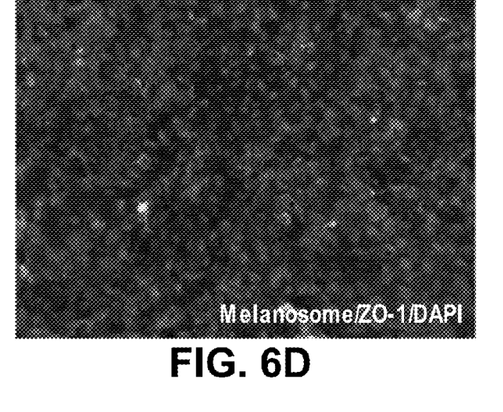
Figure 7A:
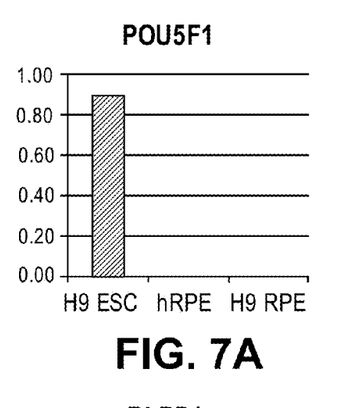
FIGS. 7A-F show RT-PCR gene expression analysis of human embryonic stem cell derived retinal pigmented epithelial cells (hESC-derived RPE) for RPE specific genes: (A) POU5F1, (B) BEST1, (C) OTX2, (D) RLBP1, (E) RPE65 and (F) SERPINF1.
Figure 7B:
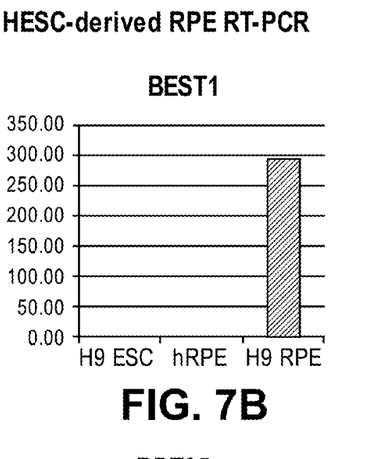
Figure 7C:
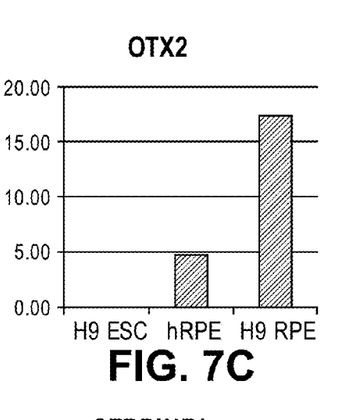
Figure 7D:
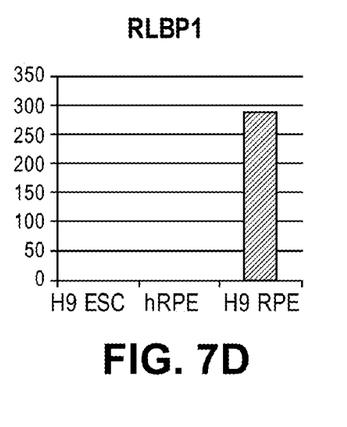
Figure 7E:
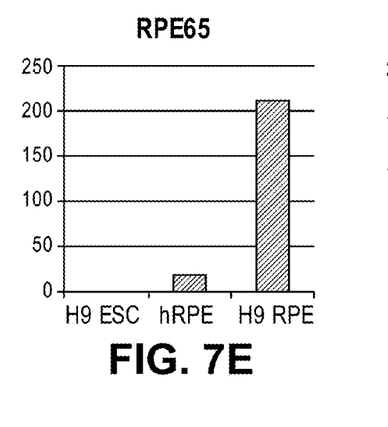
Figure 7F:
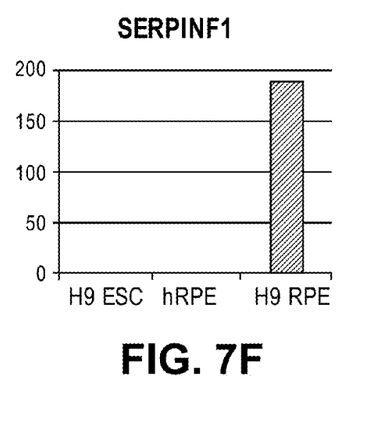

Derivation of Retinal Pigmented Epithelium from hPSCs in 3D Culture hPSCs cells growing under feeder-free culture conditions were dissociated with Accutase and grown in suspension in Ultra-low 6 well plates, with N2/B27 medium (DMEM/F12 with GlutaMAX, 1×N2/B27 Supplement) plus SB431542 (10 μM), IWR-1 (3 DMH-1 (2 μM), and Y-27632 (10 μM) for 12 days (FIG. 1) to generate retinal epithelial progenitor cells. After 12 days, to differentiate the retinal epithelial progenitor cells into retinal pigmented epithelium into RPEs, hPSC 3D cultures were switch into N2/B27 medium containing Chir99021 (3 μM) for 15 days (FIGS. 1 and 2). Chir99021 promotes the maturation/pigmentation of retinal epithelial progenitor cells. Derivation of RPEs was confirmed by immunohistochemistry for RPE specific protein expression (MITF, ZO-1, Best-1 and Melanosome) and by RT-PCR gene analysis for RPE specific gene markers (POU5F1, BEST1, OTX2, RLBP1, RPE65 and SERINF1) (FIGS. 3 and 4). FACS analysis was performed to determine the percentage of cells positive for RPE specific proteins MITF, Mel and BEST (FIG. 5).

Example 3

Derivation of Retinal Pigmented Epithelium from hESCs in 3D Culture

Figure 8A:
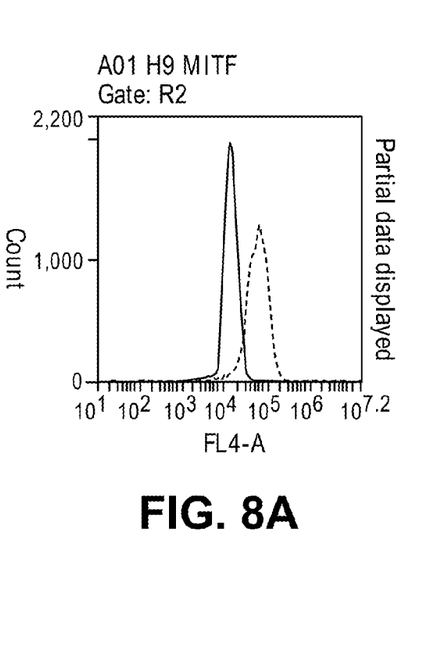
FIGS. 8A-C show purity assessment of hESC derived retinal pigmented epithelial cells (hESC-derived RPE) by FACs analysis for RPE-specific proteins (A) MITF, (B) Mel and (C) BEST (left curves), Isotype control (right curves).
Figure 8B:
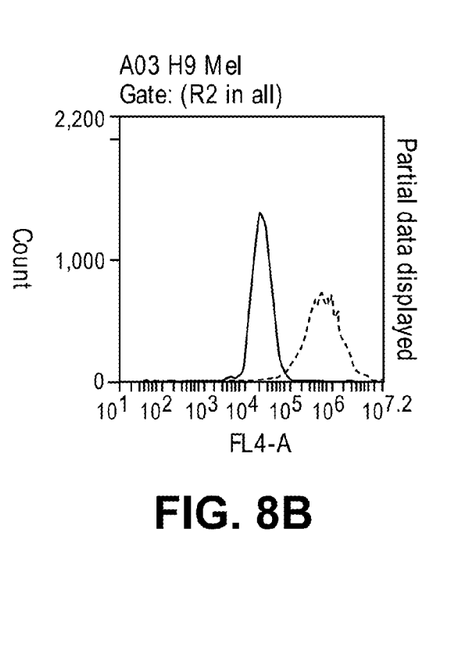
Figure 8C:
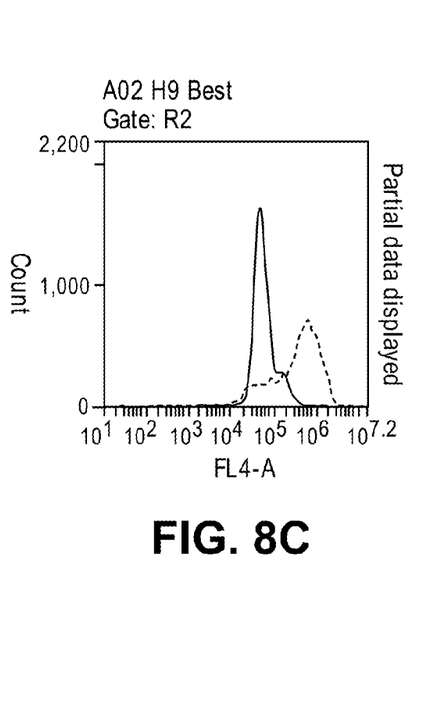
Figure 9A:
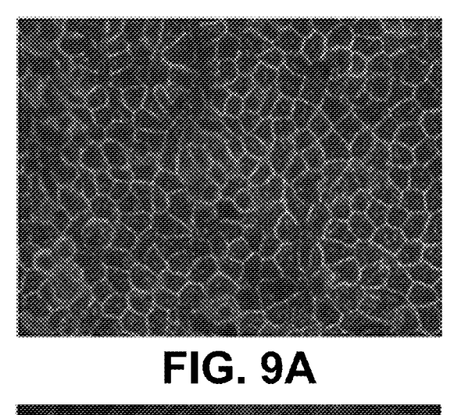
FIGS. 9A-D show protein expression analysis of induced pluripotent stem cell derived retinal pigmented epithelium (IPSC-derived RPE). A. Phase-Contrast image of a culture of IPSC-derived RPE after chemical differentiation. B-D. Immunocytochemistry images of IPSC-derived RPE cells stained for RPE-specific marker protein expression (B) MITF, and ZO-1, (C) Best-1 and ZO-1, and (D) Melanosome and ZO-1.
Figure 9B:
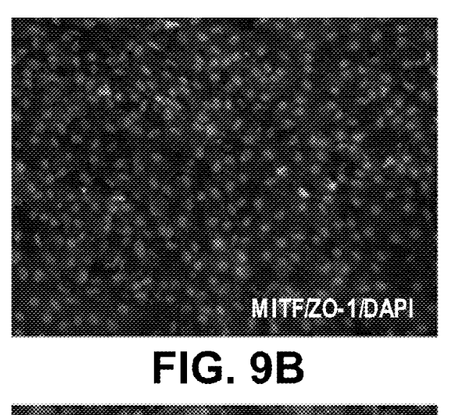
Figure 9C:
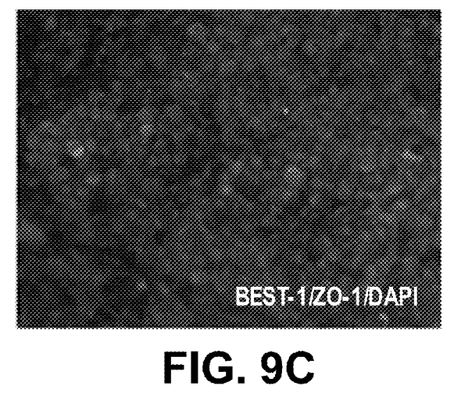
Figure 9D:
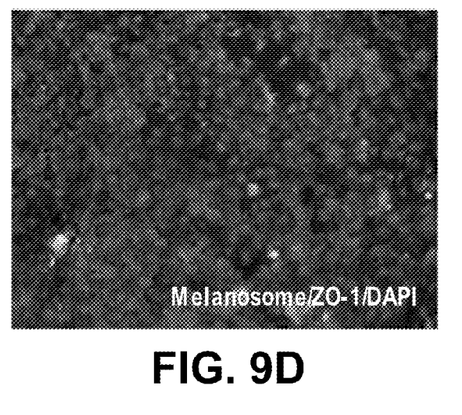
Figure 10A:
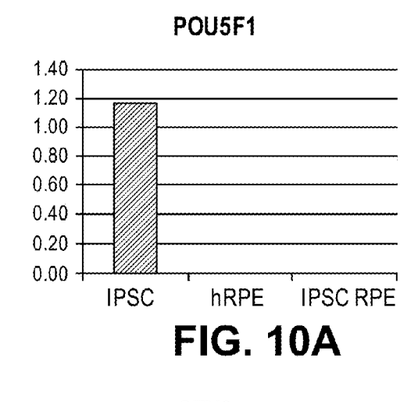
FIGS. 10A-F show RT-PCR gene expression analysis of induced pluripotent stem cell derived retinal pigmented epithelial cells (IPSC-derived RPE) for RPE specific genes: (A) POU5F1, (B) BEST1, (C) MITF, (D) OTX2, (E) RLBP1 and (F) RPE65.
Figure 10B:
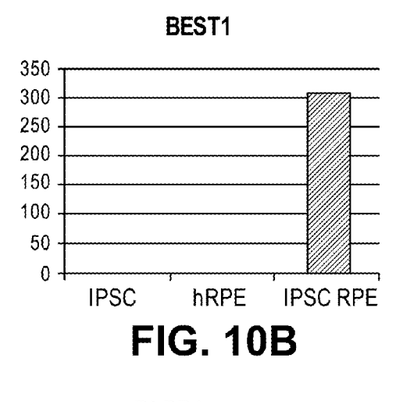
Figure 10C:
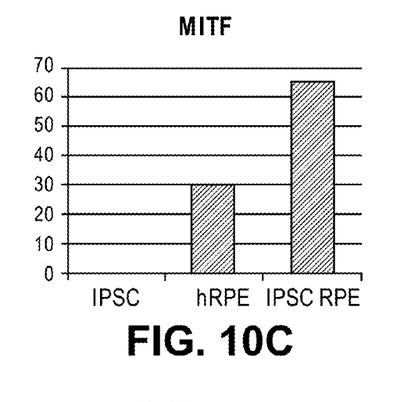
Figure 10D:
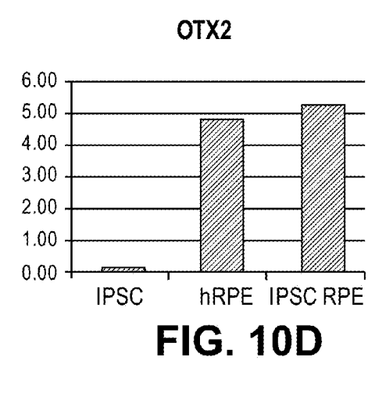
Figure 10E:
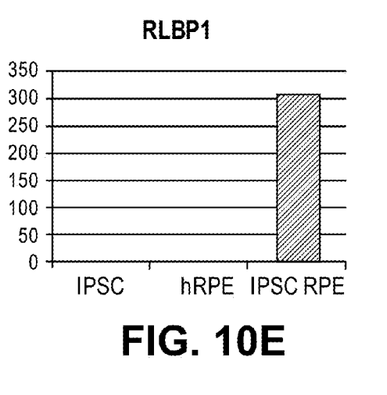
Figure 10F:
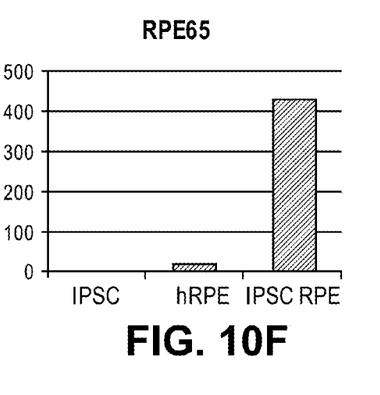

Human embryonic stem cells (hESCs) cells growing under feeder-free culture conditions were dissociated with Accutase and grown in suspension in Ultra-low 6 well plates, with N2/B27 medium (DMEM/F12 with GlutaMAX, 1×N2/B27 Supplement) plus SB431542 (10 μM), IWR-1 (3 μM), DMH-1 (2 μM), and Y-27632 (10 μM) for 12 days (FIG. 1) to generate retinal epithelial progenitor cells. After 12 days, to differentiate the retinal epithelial progenitor cells into RPEs, hESC 3D cultures were switch into N2/B27 medium containing Chir99021 (3 μM) for 15 days. Phase contrast images confirmed the derivation of RPE from hESCs after chemical differentiation (FIG. 6). Derivation of RPEs was also confirmed by RT-PCR gene analysis for specific RPE gene markers POU5F1, BEST1, OTX2, RLBP1, RPE65 and SERINF1 (FIG. 7). FACS analysis was performed to determine the percentage of cells positive for RPE specific proteins MITF, Mel and BEST (FIG. 8).

Example 4

Derivation of Retinal Pigmented Epithelium from IPSCs in 3D Culture

Figure 11A:
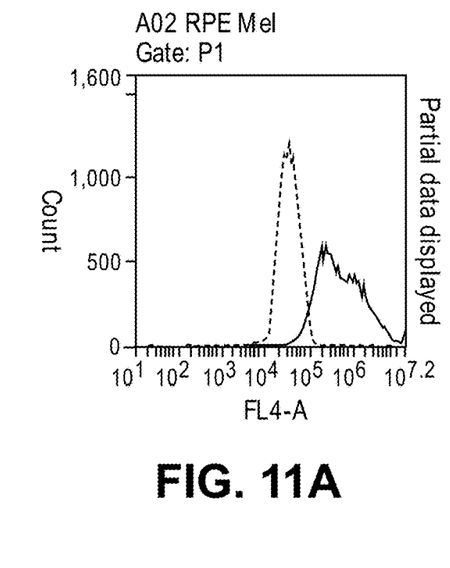
FIGS. 11A-C show the purity assessment of IPSC derived retinal pigmented epithelial cells (IPSC-derived RPE) by FACs analysis for RPE-specific proteins (A) MITF, (B) Mel and (C) BEST (right curves), Isotype control (left curves).
Figure 11B:
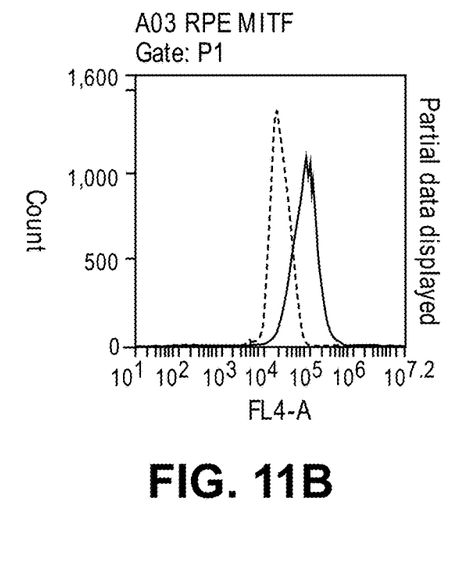
Figure 11C:
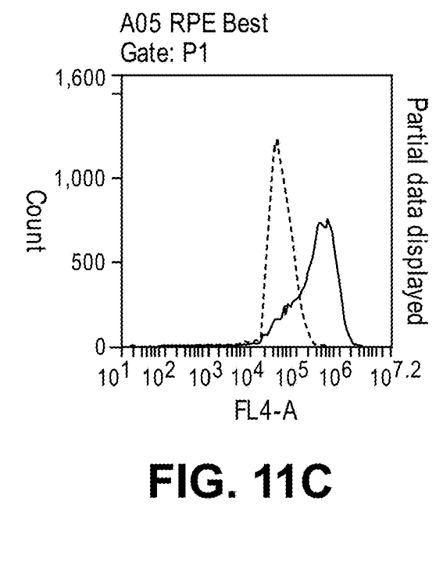

Induced pluripotent stem cells (IPSCs) cells growing under feeder-free culture conditions were dissociated with Accutase and grown in suspension in Ultra-low 6 well plates, with N2/B27 medium (DMEM/F12 with GlutaMAX, 1×N2/B27 Supplement) plus SB431542 (10 μM), IWR-1 (3 μM), DMH-1 (2 μM), and Y-27632 (10 μM) for 12 days (FIG. 1) to generate retinal epithelial progenitor cells. After 12 days, to differentiate the retinal epithelial progenitor cells into RPEs, IPSC 3D cultures were switch into N2/B27 medium containing Chir99021 (3 μM) for 15 days. Phase contrast images confirmed the derivation of RPE from IPSCs after chemical differentiation (FIG. 9). Derivation of RPEs was also confirmed by RT-PCR gene analysis for specific RPE gene markers POU5F1, BEST1, MITF, OTX2, RLBP1 and RPE65 (FIG. 10). FACS analysis was performed to determine the percentage of cells positive for RPE specific proteins MITF, Mel and BEST (FIG. 11).

Although the invention has been described with reference to the above examples, it will be understood that modifications and variations are encompassed within the spirit and scope of the invention. Accordingly, the invention is limited only by the following claims.

What is claimed is:

1. A method of producing retinal pigmented epithelial cells (RPEs) comprising: a) culturing human pluripotent stem cells (hpSCs) on a feeder layer; b) transferring the hpSCs to feeder layer free culture conditions; c) culturing the hpSCs simultaneously with a ROCK inhibitor, a TGFβR-1 inhibitor, a Wnt inhibitor, and a BMP inhibitor for a period of time sufficient to allow for the production of retinal epithelial progenitor cells; and d) culturing the retinal epithelial progenitor cells with a glycogen synthase kinase 3 (GSK-3) inhibitor, for a period of time sufficient to allow for the production of RPEs, wherein the RPEs express at least one RPE specific markers selected from the group consisting of POU5F1, BEST-1, MITF, OTX2, RLPB1, RPE65, SERPINF1, ZO1, MELANOSOME or a combination thereof.

2. The method of claim 1, wherein the hpSCs are selected from the group consisting of: embryonic stem cells, parthenogenetic stem cells, induced pluripotent stem cells and nuclear transfer derived stem cells.

3. The method of claim 1, wherein the feeder layer comprises mitomycin-C inactivated mouse embryonic fibroblast cells.

4. The method of claim 1, wherein the feeder layer free culture conditions comprise culturing the hpSCs on plates coated with a xeno-free substrate.

5. The method of claim 1, wherein the TGFβR-1 inhibitor is selected from the group consisting of A83-01, D4476, GW788388, ITD1, LY2109761, Galunisertib (LY2157299), LY364947, 8268712, RepSox, SB431542, SB505124, SB525334, SD-208 and SIS3.

6. The method of claim 1, wherein the Wnt inhibitor is selected from the group consisting of Cardionogen 1, Calphostin C, CCT031374 hydrobromide, FH535, ICG-001, iCRT14, IWP-2, IWP-4, IWP-12, IWP-L6, IWR-1, JW55, JW67, KY02111, LGK-974, MN64, PNU74654, QS11, TAK715, TC-E5001, WAY316606 hydrochloride, WIKI4, WNT-C59 and XAV-939.

7. The method of claim 1, wherein the BMP inhibitor is selected from the group consisting of Dorsomorphin, LD-193189, DMH-1 and K02288.

8. The method of claim 1, wherein the ROCK inhibitor is selected from the group consisting of AS1892802, AT13148, Fasudil (HA-1077); Glycyl-H-1152, GSK269962, GSK429286, HA-1100, H1152, Narciclasin, OXA 06, OXA06 dihydrochloride, RKI-1447, SB772077B, SR3677, Thiazovivin and Y-27632.

9. The method of claim 1, wherein the GSK-3 inhibitor is selected from the group consisting of 3F8, 1-Azakenpaullone, 10Z-Humenialdisine, Alsterpaullone, A1070722, AR-A014418, AZD1080, AZD2858, Bikinin, BIO, Cazpaullone, CT98014, CT98023, CT99021 (Chir99021), Chir98014, Dibromocantharelline, GSKJ2, HMK-32, Hymenialdesine, Indirubin, Indirubin-3'-omime, IM-12, Kenpaullone, L803, L803-mts, Lithium carbonate, LY2090314, Manzamine A, Meridianin, NCS693868, NP00111, NP031115, Palinurine, SB216763, SB415286, TCS21311, TC-G-24, TCS2002, TDZD-8, Tideglusib, Tricantine and TWS119.

10. The method of claim 1, wherein the TGFβR-1 inhibitor, Wnt inhibitor, ROCK inhibitor and BMP inhibitor comprises SB431542, IWR-1, DMH-1 or Y-27632, or any combination thereof, and the GSK-3 inhibitor comprises Chir99021.

11. The method of claim 1, wherein the hpSCs are simultaneously cultured with the ROCK inhibitor, BMP inhibitor, TGFβR-1 inhibitor and Wnt inhibitor for about 5 days, about 10 days, about 11 days, about 12 days, about 13 days, about 14 days or about 15 days.

12. The method of claim 1, the wherein the hpSCs are cultured with the GSK-3 inhibitor for about 5 days, about 10 days, about 11 days, about 12 days, about 13 days, about 14 days or about 15 days.

* * * * *